(12) United States Patent
Lee et al.

(10) Patent No.: US 7,470,530 B2
(45) Date of Patent: Dec. 30, 2008

(54) RUMEN BACTERIA VARIANTS AND PROCESS FOR PREPARING SUCCINIC ACID EMPLOYING THE SAME

(75) Inventors: Sang Yup Lee, Daejeon (KR); Sang Jun Lee, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 10/580,556

(22) PCT Filed: May 20, 2004

(86) PCT No.: PCT/KR2004/001210

§ 371 (c)(1), (2), (4) Date: May 26, 2006

(87) PCT Pub. No.: WO2005/052135

PCT Pub. Date: Jun. 9, 2005

(65) Prior Publication Data

US 2007/0054387 A1    Mar. 8, 2007

(30) Foreign Application Priority Data

Nov. 27, 2003  (KR) ............... 10-2003-0084934
Apr. 23, 2004  (KR) ............... 10-2004-0028105

(51) Int. Cl.
*C12N 1/20*   (2006.01)
*C12N 1/12*   (2006.01)
*C12N 9/10*   (2006.01)
*C12P 7/46*   (2006.01)

(52) U.S. Cl. ............... 435/252.1; 435/252.3; 435/435; 435/69.1; 435/145; 435/193; 536/23.2

(58) Field of Classification Search .............. None
See application file for complete search history.

(56) References Cited

FOREIGN PATENT DOCUMENTS

| JP | 11-206385 A | 8/1999 |
|---|---|---|
| KR | 10-0267505 B1 | 10/2000 |
| KR | 10-0372218 B1 | 2/2003 |
| WO | 9716528 A1 | 5/1997 |
| WO | 0200846 A1 | 1/2002 |

OTHER PUBLICATIONS

Chang et al. (Appld and envrn Microbiol 1999, pp. 1384-1389).*
Chatterjee, Ranjini, et al., Mutation of the ptsG Gene Results in Increased Production of Succinate in Fermentation of Glucose by *Escherichia coli* , Appl. Environ. Microbiol., Jan. 2001, pp. 148-154, vol. 67, No. 1.
Lee, P.C., et al., Batch and continuous cultivation of *Anaerobiospirillum succiniciproducens* for the production of succinic acid from whey, Appl. Microbiol. Biotechnol., Jul. 2000, pp. 23-27, vol. 54, No. 1.
Lee, Pyong Cheon, et al., Succinic acid production with reduced by-product formation in the fermentation of *Anaerobiospirillum succiniciproducens* . . . , Biotechnol. Bioeng., Nov. 6, 2000, pp. 41-48, vol. 72, No. 1.
Lee, P.C., et al., Isolation and characterization of a new succinic acid-producing bacterium, *Mannheimia succiniciproducens* MBEL55E, from . . . , Appl. Microbiol. Biotechnol., Apr. 2002, pp. 663-668, vol. 58, No. 5.
Lee, P.C., et al., Batch and continuous cultures of *Mannheimia succiniciproducens* MBEL55E for the production of succinic acid from whey and . . . , Bioprocess Biosys. Eng., Nov. 2003, pp. 63-67, vol. 26, No. 1.
Lee, P.C., et al., Biological conversion of wood hydrolysate to succinic acid by *Anaerobiospirillum succiniciproducens* , Biotechnol. Lett., Jan. 2003, pp. 111-114, vol. 25, No. 2.
Millard, Cynthia Sanville, et al., Enhanced production of succinic acid by overexpression of phosphoenolpyruvate carboxylase in *Escherichia coli* Appl. Environ. Microbiol., May 1996, pp. 1808-1810, vol. 62, No. 5.
Stols, Lucy, et al., Production of succinic acid through overexpression of NAD(+)-dependent malic enzyme in an *Escherichia coli* mutant, Appl. Environ. Microbiol., Jul. 1997, pp. 2695-2701, vol. 63, No. 7.
Vemuri, G.N., et al., Succinate production in dual-phase *Escherichia coli* fermentations depends on the time of transition from aerobic to . . . , J. Ind. Microbiol. Biotech., Jun. 2002, pp. 325-332, vol. 28, No. 6.
Vemuri, G.N., et al., Effects of Growth Mode and Pyruvate Carboxylase on Succinic Acid Production by Metabolically Engineered Strains of . . . , Appl. Environ. Microbiol., Apr. 2002, pp. 1715-1727, vol. 68, No. 4.
Chao, Yun-Peng, et al., Alteration of growth yield by overexpression of phosphoenolpyruvate carboxylase and phosphoenolpyruvate carboxykinase . . . , Appl. Environ. Microbiol., Dec. 1993, pp. 4261-4265, vol. 59, No. 12.
Davis, C.P., *Anaerobiospirillum*, a new genus of spiral-shaped bacteria, Int. J. Sys. Bacteriol., Oct. 1976, pp. 498-504, vol. 26, No. 4.
Zeikus, J.G., Chemical and fuel production by anaerobic bacteria, Ann. Rev. Microbiol., 1980, pp. 423-464, vol. 34.

(Continued)

*Primary Examiner*—Tekchand Saidha
*Assistant Examiner*—MD. Younus Meah
(74) *Attorney, Agent, or Firm*—Kelly Reynolds; Intellectual Property/ Technology Law; Steven J. Hultquist

(57) ABSTRACT

Provided are novel rumen bacterial mutants resulted from the disruption of a lactate dehydrogenase gene (ldhA) and a pyruvate formate-lyase gene (pfl) from rumen bacteria; a novel bacterial mutant (*Mannheimia* sp. LPK7) having disruptions of a ldhA, a pfl, a phosphotransacetylase gene (pta), and a acetate kinase gene (ackA); a novel bacterial mutant (*Mannheimia* sp. LPK4) having disruptions of a ldhA, a pfl, and a phosphoenolpyruvate carboxylase gene (ppc) involved in the immobilization of $CO_2$ in a metabolic pathway of producing succinic acid; and a method for producing succinic acid, characterized by culture of the above mutants in anaerobic conditions. The bacterial mutants have the property of producing succinic acid at high concentration while producing little or no organic acids, as compared to the prior wild-type strains of producing various organic acids. Thus, the bacterial mutants are useful as strains for the industrial production of succinic acid.

9 Claims, 12 Drawing Sheets

OTHER PUBLICATIONS

Kim, Pil, et al., "Effect of overexpression of *Actinobacillus succinogenes* phosphoenolpyruvate carboxykinase on succinate production in . . . ", "Applied and Environmental Microbiology", Feb. 2004, pp. 1238-1241, vol. 70, No. 2.

Laivenieks, M., et al., "Cloning, sequencing, and overexpression of the *Anaerobiospirillum succiniciproducens* phosphoenolpyruvate carboxykinase . . . ", "Appl. Environ. Microbiol.", Jun. 1997, pp. 2273-2280, vol. 63, No. 6.

McKinlay, James B., et al., "Prospects for a bio-based succinate industry", "Appl. Microbiol. Biotechnol.", 2007, pp. 727-740, vol. 76.

Samuelov, Nissim S., et al., "Why fermentation by *Anaerobiospirillum succiniciproducens* for production of a succinate-based animal feed additive", "Applied and Environmental Microbiology", May 1999, pp. 2260-2263, Vol. 65, No. 5.

Song, Hyohak, et al., "Production of succinic acid by bacterial fermentation", "Enzyme and Microbial Technology", 2006, pp. 352-361, vol. 39.

Van Der Werf, M. J., et al., "(Abstract) Environmental and physiological factors affecting the succinate product ratio during carbohydrate . . . ", "Arch. Microbiol.", Jun. 1997, pp. 332-342, vol. 176, No. 6.

Zeikus, J.G., et al., "Biotechnology of succinic acid production and markets for derived industrial products", "Appl. Microbiol. Biotechnol.", May 1999, pp. 545-552, vol. 51, No. 5.

\* cited by examiner

RUMEN BACTERIA VARIANTS AND PROCESS FOR PREPARING SUCCINIC ACID EMPLOYING THE SAME

CROSS-REFERENCE TO RELATED APPLICATIONS

This application is filed under the provisions of 35 U.S.C. §371 and claims the benefit of priority of International Patent Application No. PCT/KR2004/01210 filed May 20, 2004, which in turn claims priority of Korean Patent Application No. 10-2003-0084934 filed Nov. 27, 2003 and Korean Patent Application No. 10-2004-0028105 filed Apr. 23, 2004. The disclosures of all of said applications are hereby incorporated herein by reference in their respective entireties.

TECHNICAL FIELD

The present invention relates to a rumen bacterial mutant which produce succinic acid at high concentration while producing little or no other organic acids, as well as a method for producing succinic acid, which is characterized by the culture of such mutants in anaerobic conditions.

BACKGROUND ART

Various anaerobic microorganisms, including *Succinivibrio dextrinosolvens, Fibrobacter succinogenes, Ruminococcus flavefaciens* and the like, produce succinic acid as an end product by glucose metabolism (Zeikus, *Annu. Rev. Microbiol.*, 34:423, 1980). Strains that produce succinic acid at industrially useful yield have not yet been reported except for *Anaerobiospirillum succiniciproducens* known to produce succinic acid at high concentration and high yield from glucose upon the presence of excessive $CO_2$ (David et al., *Int. J Syst. Bacteriol.*, 26:498, 1976). However, since *Anaerobiospirillum succiniciproducens* is an obligate anaerobic microorganism, a fermentation process of producing succinic acid using this microorganism has a shortcoming that the process itself becomes unstable even upon exposure to a very small amount of oxygen.

To overcome this shortcoming, *Mannheimia succiniciproducens* 55E was developed that is a strain having not only resistance to oxygen but also high organic acid productivity. However, since this strain produces formic acid, acetic acid and lactic acid in addition to succinic acid, it has shortcomings in that it has low yield and costs a great deal in a purification process of removing other organic acids except succinic acid.

Recombinant *E. coli* strains for the production of succinic acid have been reported in various literatures. If the *E. coli* strains have disruptions of a gene coding for lactate dehydrogenase and a gene coding for pyruvate formate-lyase, it is hard for them to grow in anaerobic conditions. Furthermore, they have too low yield to apply them to industrial field, since, although lactic acid is not produced as a fermentation product, other metabolites (acetic acid and ethanol) account for about half of the production of succinic acid. In an attempt to overcome such shortcomings, *E. coli* cells were grown in aerobic conditions, and then anaerobic conditions were applied to induce the fermentation of succinic acid. However, this attempt still has low productivity (Vemuri et al., *J. Ind. Microbiol. Biotechnol.*, 28:325, 2002). Also, other examples were reported in which the genes of enzymes, such as pyruvate carboxylase, phosphoenolpyruvate carboxylase, phosphoenolpyruvate carboxykinase, and malic enzyme, that immobilize $CO_2$ in a metabolic pathway of succinic acid fermentation, are introduced into *E. coli*, thereby increasing the production of succinic acid (Vemuri et al., *Appl. Environ. Microbiol.*, 68:1715, 2002; Millard et al., *Appl. Environ. Microbiol.*, 62:1808, 1996; Chao and Liao, *Appl. Environ. Microbiol.*, 59:4261, 1993; Stols and Donnelly, *Appl. Environ. Microbiol.*, 63:2695, 1997).

Meanwhile, it is known that the disruption of ptsG in *E. coli* contributes to an improvement of bacterial production and succinic acid production (Chatterjee et al., *Appl. Environ. Microbiol.*, 67:148. 2001), but most of rumen bacteria have no ptsG, and thus have an advantage that they do not require a removal process of ptsG as in the case of *E. coli*. Recently, an attempt is actively conducted in which the genes of enzymes that immobilize $CO_2$ in a metabolic pathway of succinic acid fermentation are introduced into rumen bacteria, including genus *Actinobacillus* and genus *Anaerobiospirillum*. However, in this attempt, other organic acids were produced at large amounts or the yield of succinic acid was so low, as a result of that, it did not reach an industrially applicable level.

DISCLOSURE OF INVENTION

Accordingly, during our extensive studies to develop bacterial strains that produce succinic acid at high yield, the present inventors constructed bacterial mutant *Mannheimia* sp. LPK (KCTC 10558BP) by the disruption of a lactate dehydrogenase gene (ldhA) and a pyruvate formate-lyase gene (pfl) from *Mannheimia succiniciproducens* 55E, which is a kind of rumen bacteria, and constructed bacterial mutants *Mannheimia* sp. LPK7 and LPK4, by the disruption of phosphotransacetylase gene (pta) and an acetate kinase gene (ackA,), and a phosphoenolpyruvate carboxylase gene (ppc), respectively from the LPK strain, and then confirmed that the culture of such bacterial mutants in anaerobic conditions provides succinic acid at high yield, thereby completing the present invention.

Therefore, a main object of the present invention is to provide a rumen bacterial mutant that produces succinic acid at high yield while producing no other organic acids, as well as a producing method thereof.

Another object of the present invention is to provide a method of producing succinic acid, which is characterized by the culture of the above bacterial mutants in anaerobic conditions.

To achieve the above objects, in one aspect, the present invention provides a rumen bacterial mutant which a lactate dehydrogenase-encoding gene (ldhA) and a pyruvate formate-lyase-encoding gene (pfl) have been disrupted, and has the property of producing succinic acid at high concentration while producing little or no other organic acids in anaerobic conditions.

In another aspect, the present invention provides a rumen bacterial mutant which a lactate dehydrogenase-encoding gene (ldhA), a pyruvate formate-lyase-encoding gene (pfl), a phosphotransacetylase-encoding gene (pta) and a acetate kinase-encoding gene (ackA) have been disrupted, and has the property of producing succinic acid at high concentration while producing little or no other organic acids in anaerobic conditions.

In still another aspect, the present invention provides a rumen bacterial mutant which a lactate dehydrogenase-encoding gene (ldhA), a pyruvate formate-lyase-encoding gene (pfl), and a phosphoenolpyruvate carboxylase-encoding gene (ppc) have been disrupted, and has the property of producing succinic acid at high concentration while producing little or no other organic acids in anaerobic conditions.

In the present invention, the rumen bacteria are preferably homo-fermentative bacteria that may be selected from the group consisting of genus *Mannheimia*, genus *Actinobacillus* and genus *Anaerobiospirillum* and produce only succinic acid while producing little or no other organic acids. In a preferred embodiment of the present invention, the rumen bacterial mutant is *Mannheimia* sp. LPK, LPK7 or LPK4.

In still another aspect, the present invention provides a method for producing rumen bacterial mutant that has the property of producing succinic acid at high concentration while producing little or no other organic acids in anaerobic conditions, the method comprising disrupting a lactate dehydrogenase-encoding gene (ldhA) and a pyruvate formate-lyase-encoding gene (pfl) from rumen bacteria that are selected from the group consisting of genus *Mannheimia*, genus *Actinobacillus* and genus *Anaerobiospirillum*.

In the inventive method for producing the rumen bacterial mutant, the disruptions of the ldhA and pfl genes are preferably performed by homologous recombination. The homologous recombination is preferably performed using a genetic exchange vector containing a disrupted ldhA and a genetic exchange vector containing a disrupted pfl. Preferably, the vector containing a disrupted ldhA is pMLKO-sacB, and the vector containing a disrupted pfl is pMPKO-sacB.

In yet another aspect, the present invention provides a method for producing rumen bacterial mutant that has the property of producing succinic acid at high concentration while producing little or no other organic acids in anaerobic conditions, the method comprising additionally disrupting a phosphotransacetylase-encoding gene (pta) and an acetate kinase-encoding gene (ackA) from rumen bacteria that are selected from the group consisting of genus *Mannheimia*, genus *Actinobacillus* and genus *Anaerobiospirillum*, and a lactate dehydrogenase-encoding gene (ldhA) and a pyruvate formate-lyase-encoding gene (pfl) have been disrupted.

The disruptions of the pta and ackA genes are preferably performed by homologous recombination. The homologous recombination is preferably performed using a genetic exchange vector containing a disrupted pta and ackA. The genetic exchange vector containing a disrupted pta and ackA is preferably pPTA-sacB.

In yet another aspect, the present invention provides a method for producing rumen bacterial mutant that has the property of producing succinic acid at high concentration while producing little or no other organic acids in anaerobic conditions, the method comprising additionally disrupting a phosphoenolpyruvate carboxylase-encoding gene (ppc) from rumen bacteria that are selected from the group consisting of genus *Mannheimia*, genus *Actinobacillus* and genus *Anaerobiospirillum*, and a lactate dehydrogenase-encoding gene (ldhA) and a pyruvate formate-lyase-encoding gene (pfl) have been disrupted.

The disruption of the ppc gene is preferably performed by homologous recombination. The homologous recombination is preferably performed using a genetic exchange vector containing a disrupted ppc. The genetic exchange vector containing a disrupted ppc is preferably pPPC-sacB.

In the present invention, the rumen bacterial mutant having disruptions of a lactate dehydrogenase-encoding gene (ldhA) and a pyruvate formate-lyase-encoding gene (pfl) is preferably *Mannheimia* sp. LPK (KCTC 10558BP).

In yet another aspect, the present invention provides a genetic exchange vector pMLKO-sacB containing a disrupted ldhA; a genetic exchange vector pMPKO-sacB containing a disrupted pfl; a genetic exchange vector pPTA-sacB containing a disrupted pta and ackA; and a genetic exchange vector pPPC-sacB containing a disrupted ppc.

In another further aspect, the present invention provides a method for producing succinic acid, the method comprising the steps of: culturing the rumen bacterial mutants in anaerobic condition; and recovering succinic acid from the culture broth.

As used herein, the term "disruption" means that the genes encoding the enzymes are modified such that the enzymes cannot be produced.

In the present invention, each of the lactate dehydrogenase gene (ldhA) and the pyruvate formate-lyase gene (pfl) was identified from the genomic information of *Mannheimia succiniciproducens* 55E, which is a kind of rumen bacteria, and then, all the two genes were removed from *Mannheimia succiniciproducens* 55E using a vector having disruptions of the genes, thereby constructing the bacterial mutant *Mannheimia* sp. LPK (KCTC 10558BP). Next, each of pta-ackA genes and a ppc gene was disrupted from the bacterial mutant *Mannheimia* sp. LPK, thereby constructing various bacterial mutants. Then, such bacterial mutants were confirmed to produce succinic acid at high concentration while producing little or no other organic acids.

The inventive bacterial mutants (*Mannheimia* sp. LPK, LPK4 and LPK7) are facultative anaerobic, gram-negative, non-mobile rods or cocobacilli, do not produce endospores, and can produce succinic acid in anaerobic conditions.

DETAILED DESCRIPTION OF THE INVENTION

The present invention will hereinafter be described in further detail by examples. It will however be obvious to a person skilled in the art that these examples are given for illustrative purpose only, and the present invention is not limited to or by the examples.

Particularly, the following examples illustrate only a method comprising disrupting genes from a genus *Mannheimia* strain to obtain bacterial mutants and then producing succinic acid at high concentration by these bacterial mutants. However, methods by which bacterial mutants having disruptions of such genes are obtained from other rumen bacterial strains, such as genus *Actinobacillus* and genus *Anaerobiospirillum*, and succinic acid is produced using the bacterial strains, will also be obvious to a person skilled in the art.

Furthermore, the following examples illustrate only a certain medium and culture method. However, the use of other mediums different from, such as whey, corn steep liquor (CSL), as described in literatures (Lee et al., *Bioprocess Biosyst. Eng.*, 26:63, 2003; Lee et al., *Appl. Microbiol. Biotechnol.*, 58:663, 2002; Lee et al., *Biotechnol. Lett.*, 25:111, 2003; Lee et al., *Appl. Microbiol. Biotechnol.*, 54:23, 2000; Lee et al., *Biotechnol. Bioeng.*, 72:41, 2001), and the use of various methods, such as fed-batch culture and continuous culture, will also be obvious to a person skilled in the art.

EXAMPLE 1

Construction of pMLKO-sacB

In order to disrupt a lactate dehydrogenase gene (ldhA) by homologous recombination, a gene exchange vector was constructed in the following manner. First, the genomic DNA of *Mannheimia succiniciproducens* 55E (KCTC 0769BP), as a template, was subjected to PCR using primers set forth in SEQ ID NO: 1 and SEQ ID NO: 2 below, and then, the obtained PCR fragment was cut with SacI and PstI and introduced into pUC18 (New England Biolabs, Inc., Beverly, Mass.), thereby constructing pUC 18-L1.

```
SEQ ID NO: 1:
5'-CAGTGAAGGAGCTCCGTAACGCATCCGCCG (LS1)

SEQ ID NO: 2:
5'-CTTTATCGAATCTGCAGGCGGTTTCCAAAA (LP1)
```

Thereafter, the genomic DNA of *Mannheimia succiniciproducens* 55E, as a template, was subjected to PCR using primers set forth in SEQ ID NO: 3 and SEQ ID NO: 4 below, and the resulting PCR fragment was cut with PstI and HindIII and introduced into the pUC18-L1, thereby constructing pUC18-L1-L2.

```
SEQ ID NO: 3:
5'-GTACTGTAAACTGCAGCTTTCATAGTTAGC (LP2)

SEQ ID NO: 4:
5'-GCCGAAAGTCAAGCTTGCCGTCGTTTAGTG (LH2)
``` pUC4K (Pharmacia, Freiburg, Germany) was cut with PstI, and the resulting kanamycin-resistant gene was fused with pUC18-L1-L2 cut with PstI, thereby constructing pUC18-L1-KmR-L2. A linker set forth in SEQ ID NO: 5 was inserted into the pUC18-L1-KmR-L2 cut with SacI, thereby making a new XbaI cutting site.

```
SEQ ID NO: 5:
5'-TCTAGAAGCT
```

Figure 1:
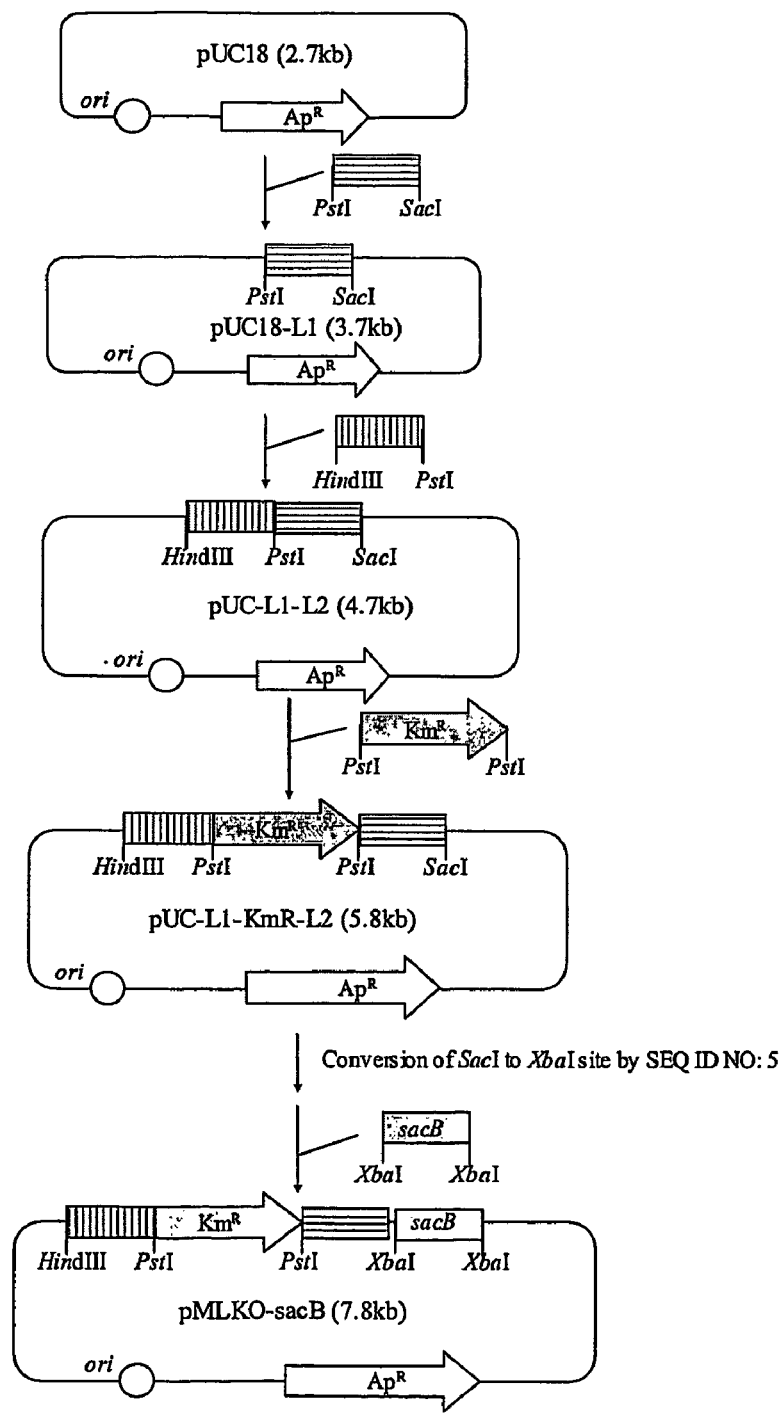
FIG. 1 shows a process of constructing a vector containing a disrupted ldhA (pMLKO-sacB).

PCR on pKmobsacB (Schafer et al, *Gene*, 145:69, 1994) as a template was performed using primers set forth in SEQ ID NO: 6 and 7 below, and the resulting PCR product was cut with XbaI and inserted into the above XbaI restriction enzyme site, thereby constructing pMLKO-sacB (FIG. 1).

```
SEQ ID NO: 6:
5'-GCTCTAGACCTTCTATCGCCTTCTTGACG (SXF)

SEQ ID NO: 7:
5'-GCTCTAGAGGCTACAAAATCACGGGCGTC (SXR)
```

EXAMPLE 2

Construction of pMPKO-sacB

In order to disrupt a pyruvate formate-lyase gene (pfl) by homologous recombination, a genetic exchange vector was constructed in the following manner. A pKmobsacB template containing a sacB gene (Genbank 02730) was subjected to PCR using primers set forth in SEQ ID NO: 8 and SEQ ID NO: 9 below. The resulting sacB product was cut with PstI and BamHI and inserted into pUC19 (Stratagene Cloning Systems. La Jolla, Calif.), thereby constructing pUC19-sacB.

```
SEQ ID NO: 8:
5'-AGCGGATCCCCTTCTATCGCCTTCTTGACG (SBG)

SEQ ID NO: 9:
5'-GTCCTGCAGGGCTACAAAATCACGGGCGTC (SPR)
```

The genomic DNA of *Mannheimia succiniciproducens* 55E, as a template, was subjected to PCR using primers set forth in SEQ ID NO: 10 and SEQ ID NO: 11 below. The resulting PCR fragment was cut with BamHI and fused with the pUC19-sacB cut with BamHI, thereby constructing pUC19-sacB-pfl.

```
SEQ ID NO: 10:
5'-CATGGCGGATCCAGGTACGCTGATTTCGAT (PB1)

SEQ ID NO: 11:
5'-CAAGGATCCAACGGATAAAGCTTTTATTAT (PB2)
```

Figure 2:
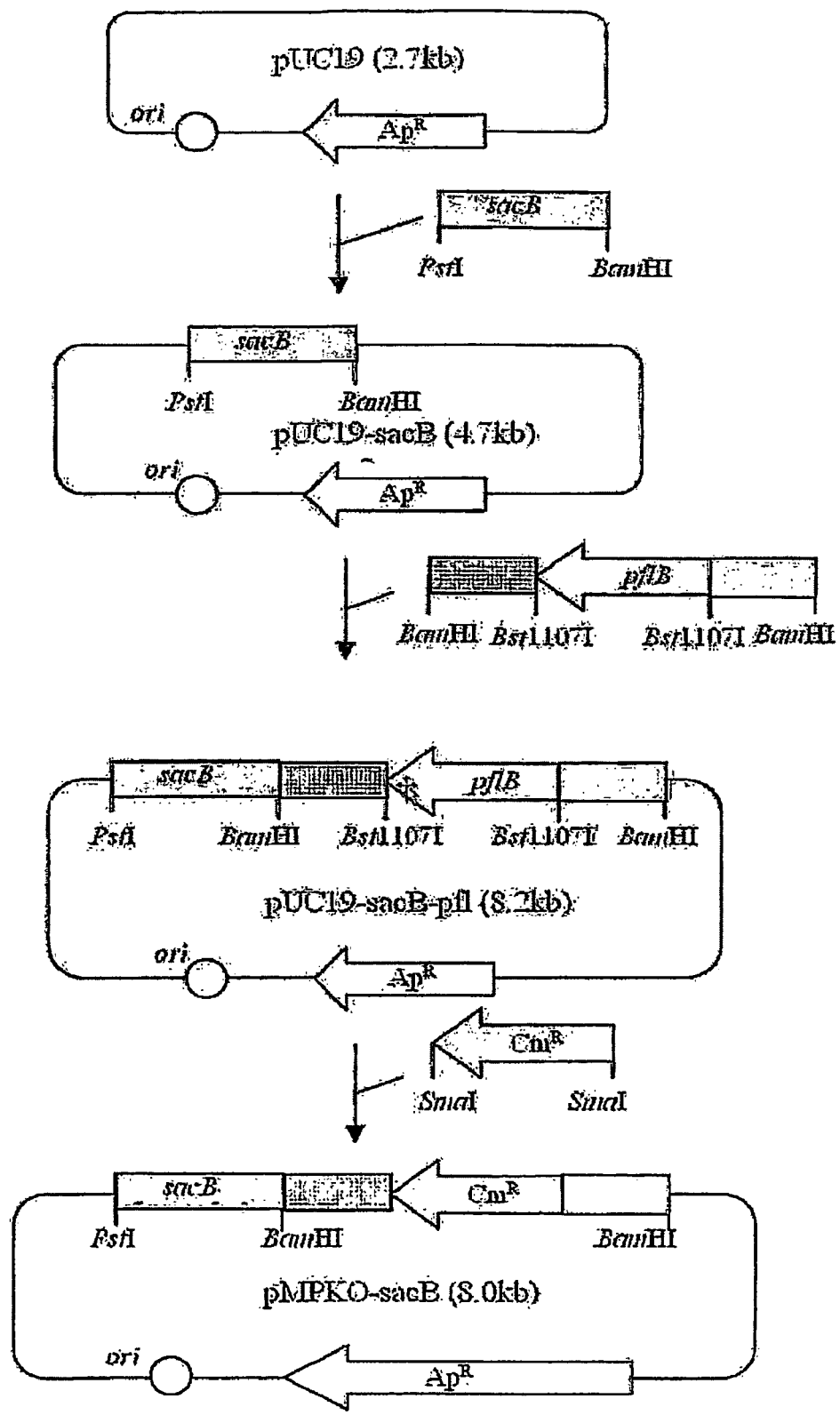
FIG. 2 shows a process of constructing a vector containing a disrupted pfl (pMPKO-sacB).

In order to obtain a chloramphenicol-resistant gene, pACYC184 (New England Biolabs, Inc., Beverly, Mass.) as a template was subjected to PCR using primers set forth in SEQ ID NO: 12 and SEQ ID NO: 13 below. The resulting PCR product was cut with SmaI and fused with the pUC19-sacB-pfl cut with Bst1107I, thereby constructing pMPKO-sacB (FIG. 2).

```
SEQ ID NO: 12:
5'-CTCGAGCCCGGGGTTTAAGGGCACCAATAA (CTR)

SEQ ID NO: 13:
5'-CTCGAGCCCCGGGCTTTGCGCCGAATAAAT (CTF)
```

EXAMPLE 3

Construction of *Mannheimia* sp. LPK Strain

Figure 3:
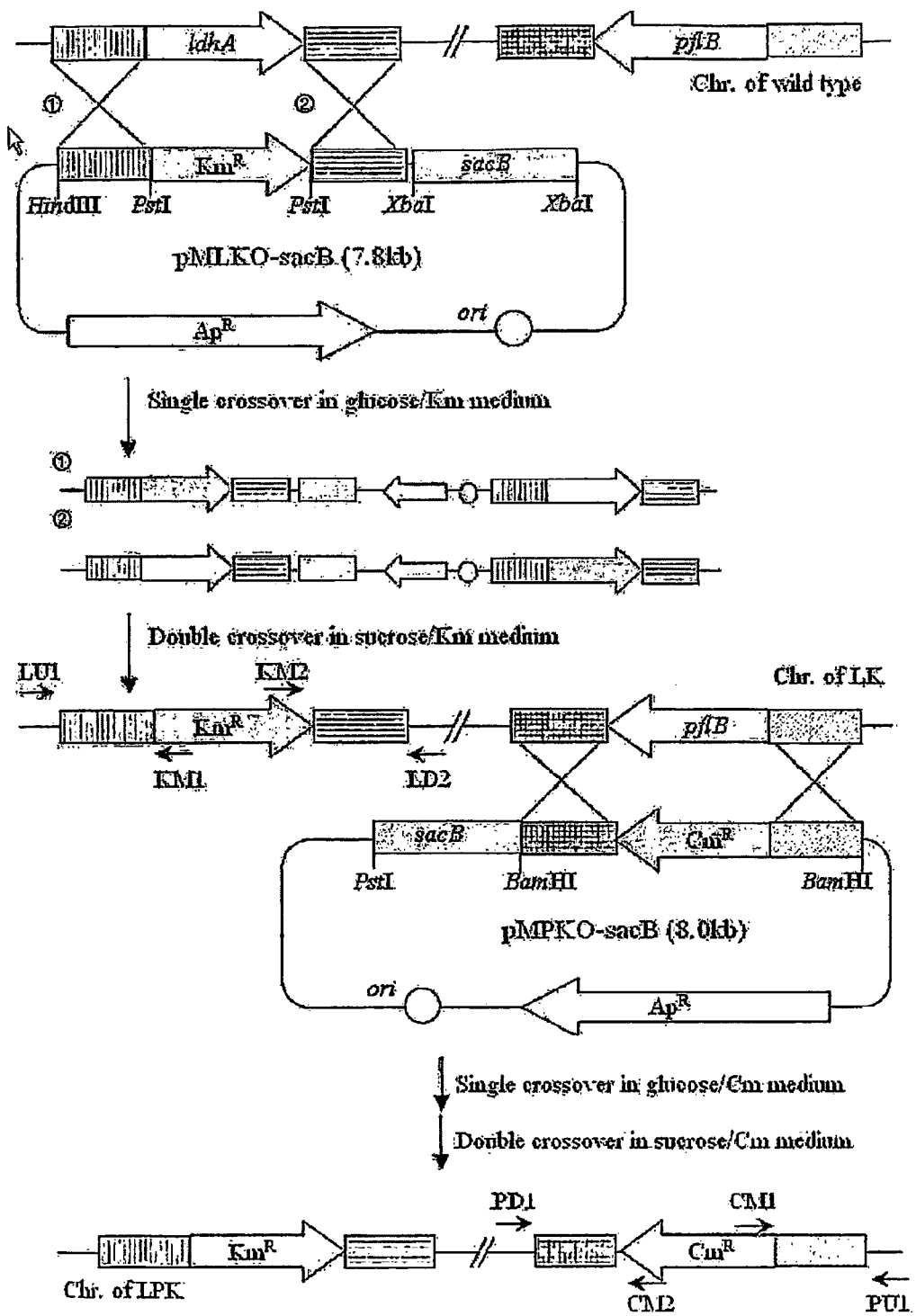
FIG. 3 shows a process of constructing a bacterial mutant (LPK) by disrupting ldhA and pfl genes from *Mannheimia succiniciproducens* 55E.

FIG. 3 shows a process of constructing a mutant strain (LPK) by disrupting ldhA and pfl genes from *Mannheimia succiniciproducens* 55E. *Mannheimia succiniciproducens* 55E was plated on LB-glucose medium containing 10 g/l of glucose, and cultured at 37° C. for 36 hours. The colony formed was inoculated in 10 ml of LB-glucose liquid medium, and cultured for 12 hours. The culture broth which had been sufficiently grown was inoculated by 1% in 100 ml of LB-glucose liquid medium, and cultured in a shaking incubator at 200 rpm and 37° C.

When the culture broth reached an OD of about 0.2-0.3 after 4~5 hours, it was centrifuged at 4° C. and 4000 rpm for 10 minutes to collect cells. Then, the cells were resuspended in 200 ml of 10% glycerol solution at 4° C. The suspension was centrifuged at 4° C. and 4000 rpm for 10 minutes, and the cells were collected and resuspended in 200 ml of 10% glycerol solution at 4° C., and then centrifuged at 4° C. and 4000 rpm for 10 minutes to collect the cells. The cells were suspended in glycerol at a volume ratio of 1:1, to obtain cell concentrate.

The cell concentrate thus obtained was mixed with the genetic exchange vectors pMLKO-sacB and pMPKO-sacB constructed in Examples 1 and 2, and then subjected to electroporation under conditions of 1.8 kV, 25 µF and 200 ohms. 1 ml of LB-glucose liquid medium was added to the electroporated mixture and cultured in a shaking incubator at 37° C. and 200 rpm for one hour. The culture broth was plated on LB-glucose solid medium containing a suitable antibiotic [Km (final concentration of 25 µg/ml) or Cm (6.8 µg/ml) and cultured at 37° C. for 48 hours or more. In order to select a colony where only double crossover occurred, the colonies formed were streaked on LB-sucrose medium (LB medium with 100 g/l sucrose) containing Km 25 µg/ml) or Cm (6.8 µg/ml). After 24 hours, the formed colonies were streaked again on the same plate.

The colony (mutant) formed on the plate were cultured in LB-glucose liquid medium containing an antibiotic, and a genomic DNA was isolated from the cultured strain by the method described in Rochelle et al. (*FEMS Microbiol. Lett.,* 100:59, 1992). PCR was performed using the isolated mutant genomic DNA as a template, and the PCR product was electrophoresed to confirm the disruption of ldhA and pfl genes from the PCR product.

In order to confirm the disruption of the ldhA gene, PCRs were performed twice in the following manners. First, the mutant genomic DNA as a template was subjected to PCR using primers set forth in SEQ ID NO: 14 and SEQ ID NO: 15.

SEQ ID NO: 14:
5'-GACGTTTCCCGTTGAATATGGC (KM1)

SEQ ID NO: 15:
5'-CATTGAGGCGTATTATCAGGAAAC (LU1)

Figure 4:
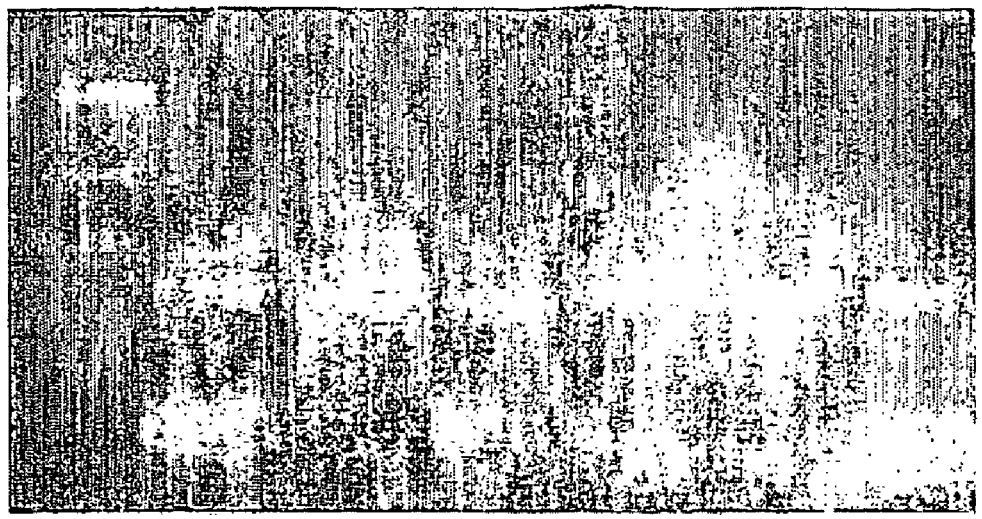
FIG. 4 is an electrophoresis photograph showing the disruption of ldhA and pfl genes from *Mannheimia* sp. LPK (M: lambda HindIII size marker; lanes 1-3: PCR product LU1 & KM1 (1.5 kb); lanes 4-6: PCR product LD2 & KM2 (1.7 kb); lanes 7-9: PCR product PU1 & CM1 (2.2 kb); and lanes 10-12: PCR product PD2 & CM2 (1.6 kb)).
Figure 4:
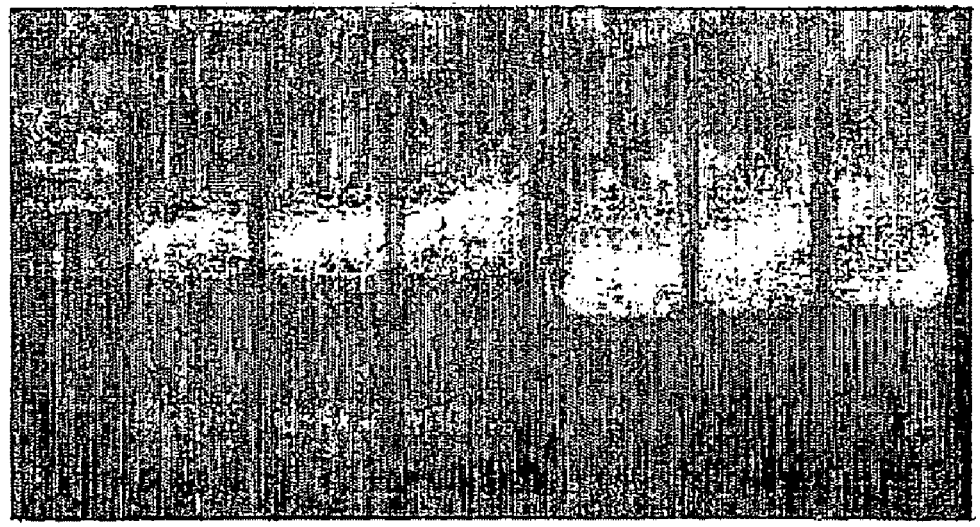

Then, the mutant genomic DNA as a template was subjected to PCR using primers set forth in SEQ ID NO: 16 and SEQ ID NO: 17 below. The products obtained in the two PCRs were subjected to gel electrophoresis to confirm the disruption of ldhA by their size (1.5 kb) (FIG. 4).

SEQ ID NO: 16:
5'-GCAGTTTCATTTGATGCTCGATG (KM2)

SEQ ID NO: 17:
5'-CCTCTTACGATGACGCATCTTTCC (LD2)

In order to confirm the disruption of pfl, PCRs were performed twice in the following manner. First, the mutant genomic DNA as a template was subjected to PCR using primers set forth in SEQ ID NO: 18 and SEQ ID NO: 19 below.

SEQ ID NO: 18:
5'-GGTGGTATATCCAGTGATTTTTTCTCCAT (CM1)

SEQ ID NO: 19:
5'-CTTTGCAACATTATGGTATGTATTGCCG (PU1)

Then, the mutant genomic DNA as a template was subjected to PCR using primers set forth in SEQ ID NO: 20 and SEQ ID NO: 21. The products obtained in the two PCRs were subjected to gel electrophoresis to confirm the disruption of pfl by their size (1.5 kb) (FIG. 4). In FIG. 4, M represents a Lambda HindIII size marker, lanes 1-3 represent the PCR product LU1 & KM1 (1.5 kb), lanes 4-6 represent the PCR product LD2 & KM2 (1.7 kb), lanes 7-9 represent the PCR product PU1 & CM1 (2.2 kb), and lanes 10-12 represent the PCR product PD2 & CM2 (1.6 kb).

SEQ ID NO: 20:
5'-TACTGCGATGAGTGGCAGGGCGGGGCGTAA (CM2)

SEQ ID NO: 21:
5'-CCCCAGCATGTGCAAATCTTCGTCAC (PD2)

The disruption of ldhA was confirmed by the fact that the product resulted from the PCR using the primers (LU1 and KM1) of SEQ ID NO: 14 and SEQ ID NO: 15 has a size of 1.5 kb an at the same time the product resulted from the PCR using the primers (LD2 and KM2) of SEQ ID NO: 16 and SEQ ID NO: 17 has a size of 1.7 kb. And, the disruption of pfl was confirmed by the fact that the product resulted from the PCR using the primers (PU1 and CM1) of SEQ ID NO: 18 and SEQ ID NO: 19 has a size of 2.2 kb and at the same time the product resulted from the PCR using the primers (PD2 and CM2) of SEQ ID NO: 20 and SEQ ID NO: 21 has a size of 1.6 kb. The position of each primer is shown in FIG. 3. The mutant constructed by the above method, i.e., a bacterial mutant having disruptions of ldhA and pfl, was named "*Mannheimia* sp. LPK" and deposited under accession number KCTC 10881BP on Nov. 26, 2003 in the Korean Collection for Type Cultures (KCTC), Korean Research Institute of Bioscience and Biotechnology (KRIBB).

EXAMPLE 4

Fermentation Characteristics of *Mannheimia* sp. LPK

In order to examine the fermentation characteristics of *Mannheimia* sp. LPK constructed in Example 3 above, the mutant was cultured in anaerobic conditions saturated with $CO_2$, and the resulting reaction product was analyzed. First, carbon dioxide was introduced into 100 ml of preculture medium consisting of 20 g/L glucose, 5 g/L polypeptone, 5 g/L yeast extract, 3 g/L $K_2HPO_4$, 1 g/L NaCl, 1 g/L $(NH_4)_2SO_4$, 0.2 g/L $CaCl_2.2H_2O$, 0.2 g/L $MgCl_2.6H_2O$ and 10 g/L MgCO$_3$, and then, *Mannheimia* sp. LPK was inoculated in the preculture medium and precultured at 39° C. for 14 hours. Then, 0.9 L of culture medium consisting of 20 g/L glucose, 5 g/L polypeptone, 5 g/L yeast extract, 3 g/L K$_2$HPO$_4$, 1 g/L NaCl, 5 g/L (NH$_4$)$_2$SO$_4$, 0.2 g/L CaCl$_2$.2H$_2$O, 0.2 g/L MgCl$_2$.6H$_2$O and 5 g/L Na$_2$CO$_3$ was put in a 2.5-L culture tank, and 100 ml of the precultured microorganisms were inoculated in the culture medium and batch-cultured at 39° C. and pH 6.5 while supplying carbon dioxide at a flow rate of 0.25 vvm.

Figure 5:
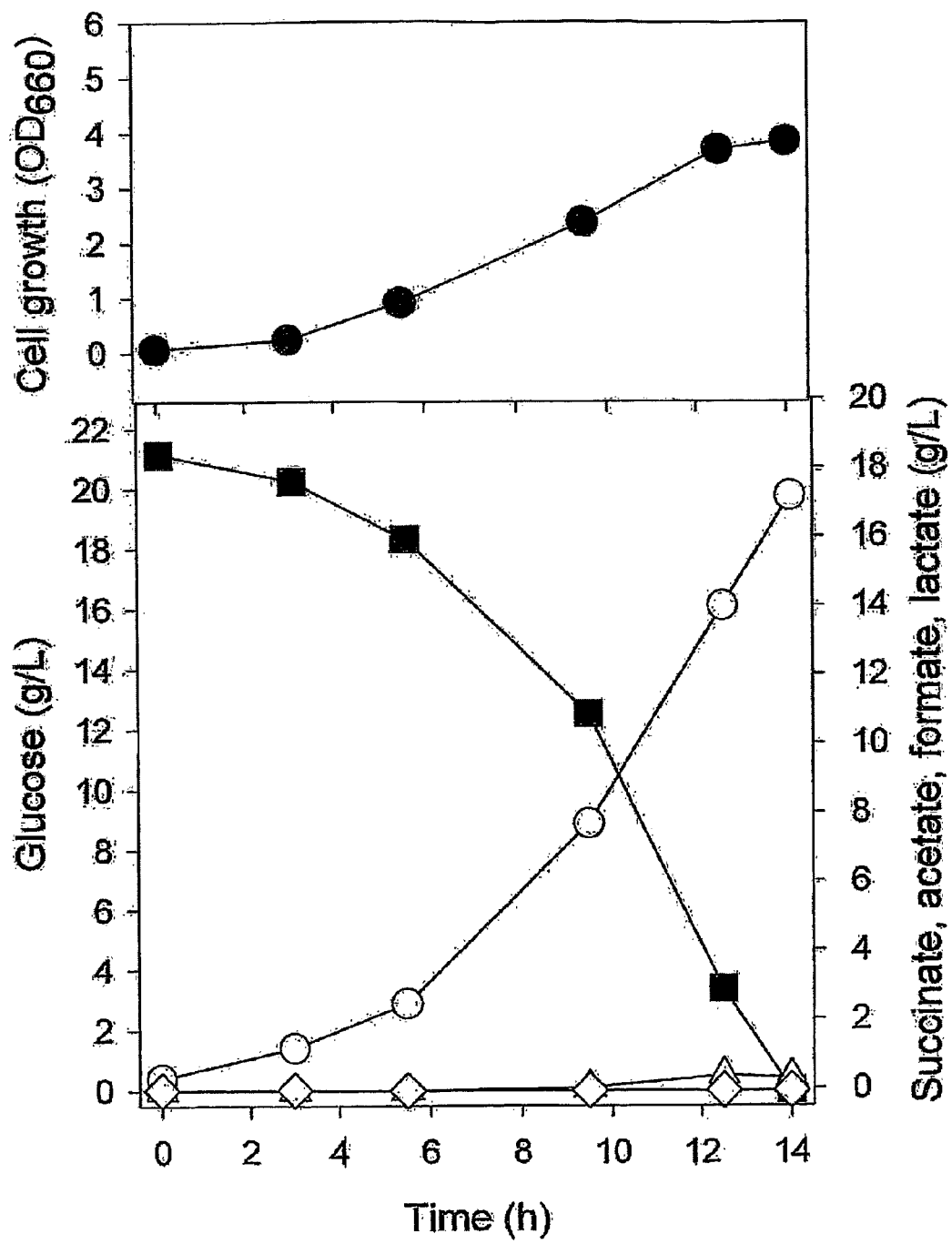
FIG. 5 shows the culture characteristics of *Mannheimia* sp. LPK in anaerobic conditions saturated with $CO_2$.

The concentration of cells in the culture broth was measured with a spectrophotometer (Ultraspec 3000, Pharmacia Biotech., Sweden), and the amounts of succinate, glucose, lactate, acetate and formate were measured by HPLC (Aminex HPX-87H column, Bio-Rad, USA) (FIG. 5). Symbols in FIG. 5, refer to changes in the concentrations of cells (●), succinate (○), glucose (■), formate (◇) and acetate (Δ) with the passage of culture time. As shown in FIG. 5, after 14 hours of culture, the concentration of consumed glucose was 20 g/L and the concentration of produced succinate was 17.2 g/L, indicating that the yield of succinate (the amount of produced succinate/the amount of consumed glucose) is 81% and the volume productivity of succinate (the concentration of produced succinate/elapsed time) is 1.23 g/L/h. The inventive method of producing succinic acid by culturing *Mannheimia* sp. LPK in anaerobic conditions saturated with CO$_2$ showed a great increase in yield as compared to that of producing succinic acid by culturing parent strain *Mannheimia succiniciproducens* 55E in anaerobic conditions saturated with CO$_2$, and showed a ratio of succinic acid: acetic acid of 40.7:1, indicating that it can produce succinic acid with little or no by-products.

EXAMPLE 5

Construction of pPTA-sacB

In order to disrupt a phosphotransacetylase gene (pta) and an acetate kinase gene (ackA) by homologous recombination, a genetic exchange vector was constructed in the following manner. First, the genomic DNA of *Mannheimia* sp. LPK (KCTC 10558BP), as a template, was amplified by PCR using primers set forth in SEQ ID NO: 22 and SEQ ID NO: 23 below, and the resulting PCR fragment was cut with XbaI and BamHI and introduced into pUC19, thereby constructing pUC19-PTA1.

```
SEQ ID NO: 22:
5'-GCTCTAGATATCCGCAGTATCACTTTCTGCGC

SEQ ID NO: 23:
5'-TCCGCAGTCGGATCCGGGTTAACCGCACAG
```

Thereafter, the genomic DNA of *Mannheimia* sp. LPK as a template was amplified by PCR using primers set forth in SEQ ID NO: 24 and SEQ ID NO: 25 below, and the resulting PCR fragment was cut with XbaI and SacI and introduced into the pUC19-PTA1, thereby constructing pUC19-PTA12.

```
SEQ ID NO: 24:
5'-GGGGAGCTCGCTAACTTAGCTTCTAAAGGCCATGT TTCC

SEQ ID NO: 25:
5'-GCTCTAGATATCCGGGTCAATATCGCCGCAAC
```

Figure 6:
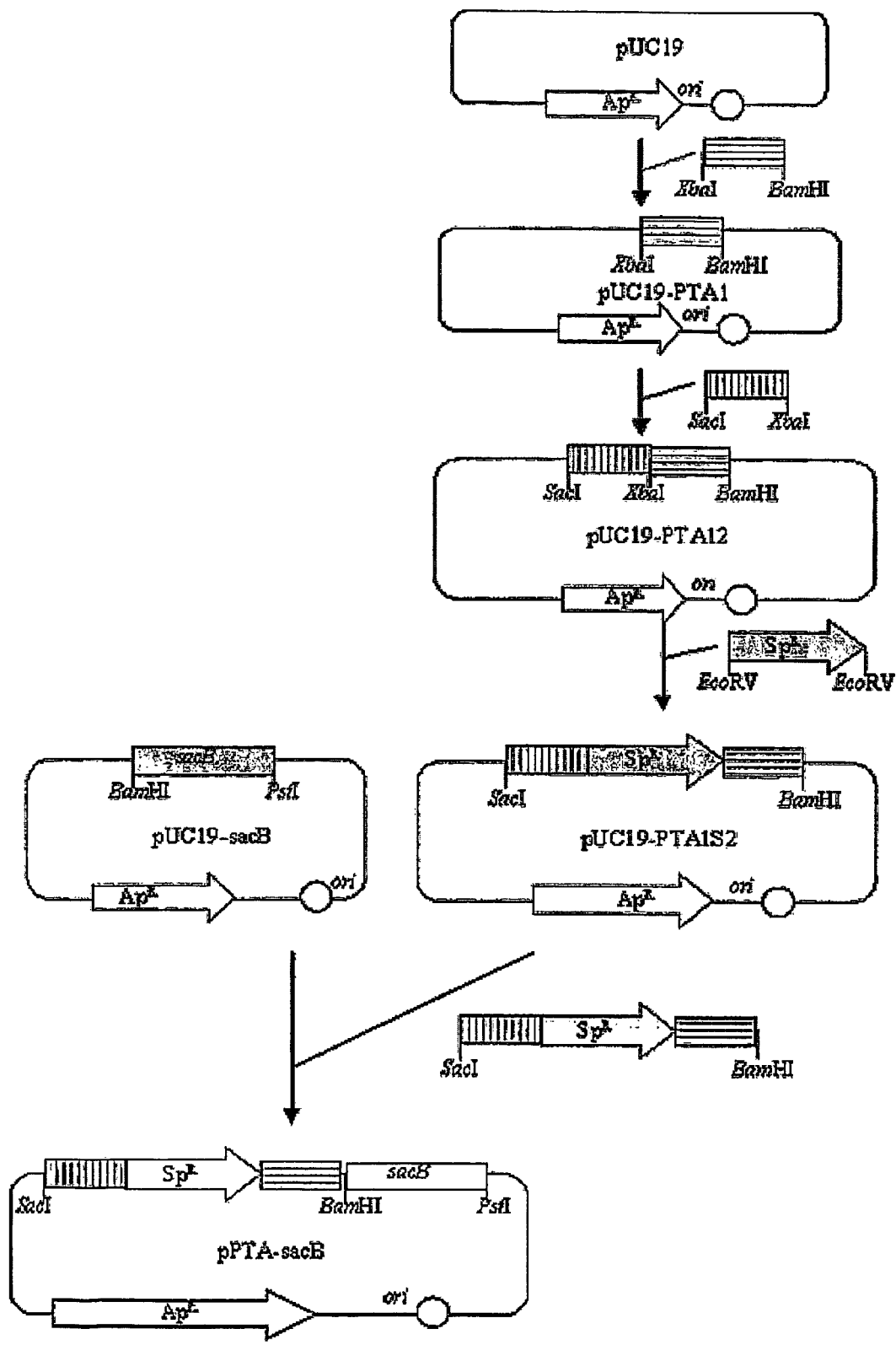
FIG. 6 shows a process of constructing vector containing a disrupted pta and ackA (pPTA-sacB).

As a template, plasmid pIC156 (Steinmetz et al., *Gene*, 142:79, 1994) containing a spectinomycin-resistant gene (GenBank X02588) was amplified by PCR using primers set forth in SEQ ID NO: 26 and SEQ ID NO: 27 below, and the resulting PCR fragment (spectinomycin-resistant gene) was cut with EcoRV and introduced into the pUC19-PTA12, thereby constructing pUC19-PTA1S2 having the spectinomycin-resistant gene. The constructed pUC19-PTA1S2 was cut with SacI and BamHI and introduced into pUC19-SacB (see Example 2), thereby constructing a pPTA-sacB vector (FIG. 6).

```
SEQ ID NO: 26:
5'-GAATTCGAGCTCGCCCGGGGATCGATCCTC

SEQ ID NO: 27:
5'-CCCGGGCCGACAGGCTTTGAAGCATGCAAATGTCAC
```

EXAMPLE 6

Construction of pPPC-sacB

In order to disrupt a phosphoenolpyruvate carboxylase gene (ppc) by homologous recombination, a genetic exchange vector was constructed in the following manner. First, the genomic DNA of *Mannheimia* sp. LPK, as a template, was amplified by PCR using primers set forth in SEQ ID NO: 28 and SEQ ID NO: 29, and the resulting PCR fragment was cut with XbaI and BamHI and introduced into pUC19, thereby constructing pUC19-PPC1.

```
SEQ ID NO: 28:
5'-TACGGATCCCCAGAAAATCGCCCCCATGCCGA

SEQ ID NO: 29:
5'-GCTCTAGATATCGTTTGATATTGTTCCGCCACATTTG
```

Thereafter, the genomic DNA of *Mannheimia* sp. LPK, as a template, was subjected to PCR using primers set forth in SEQ ID NO: 30 and SEQ ID NO: 31, and the resulting PCR fragment was cut with XbaI and SacI and introduced into the pUC19-PPC1, thereby constructing pUC19-PPC12.

```
SEQ ID NO: 30:
5'-GCTCTAGATATCCGTCAGGAAAGCACCCGCCATAGC

SEQ ID NO: 31:
5'-GGGGAGCTCGTGTGGCGCTGCGGAAGTAAGGCAAAAATC
```

Figure 7:
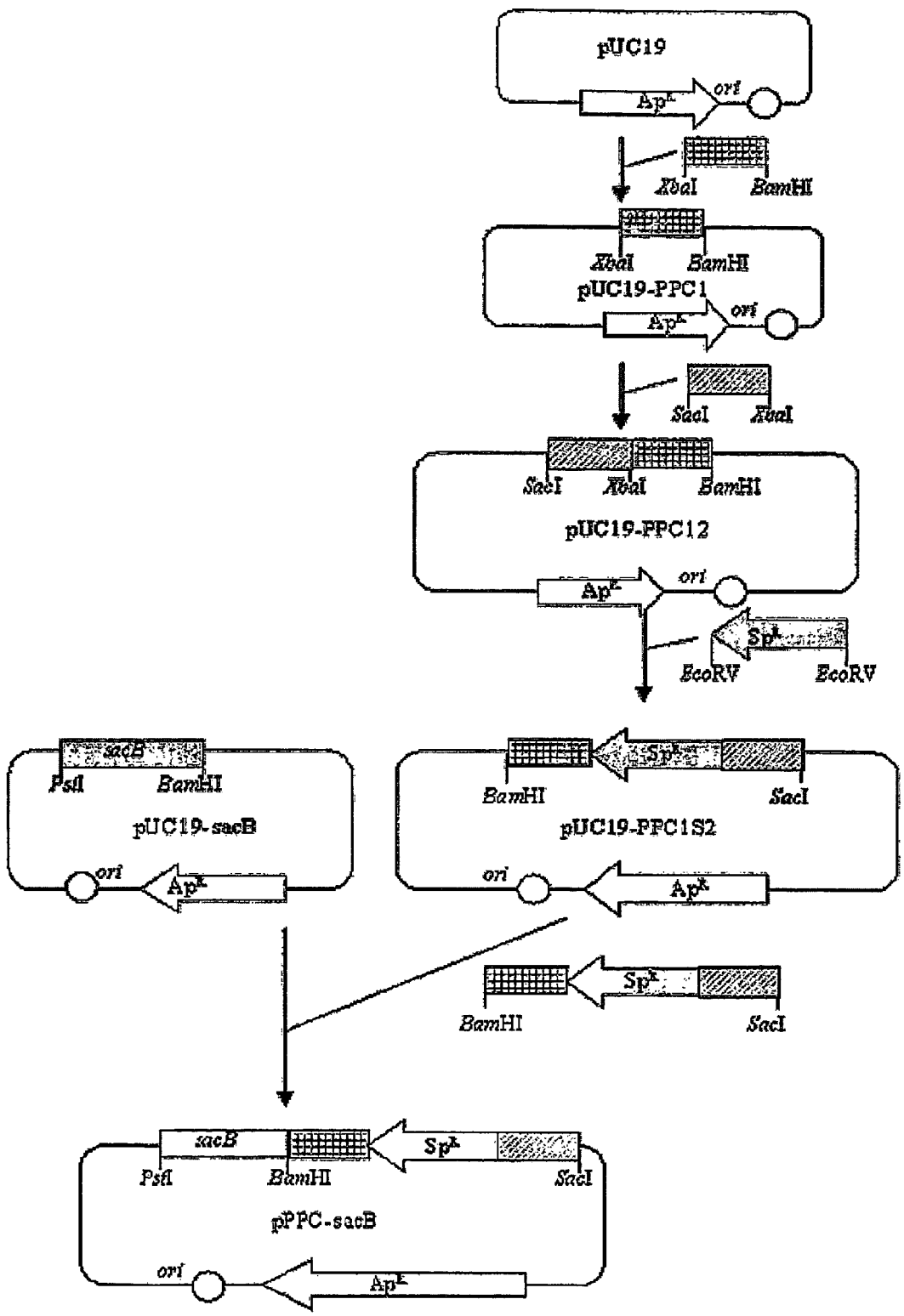
FIG. 7 is a process of constructing a vector containing a disrupted ppc (pPPC-sacB).

A spectinomycin-resistant gene cut with EcoRV (see Example 5) was introduced into the pUC19-PPC12 to construct pUC19-PPC1S2. The pUC19-PPC1S2 was cut with SacI and BamHI and introduced into the pUC19-SacB, thereby constructing a pPPC-sacB vector (FIG. 7).

EXAMPLE 7

Construction of *Mannheimia* sp. LPK7 and LPK4 Strains

Figure 8:
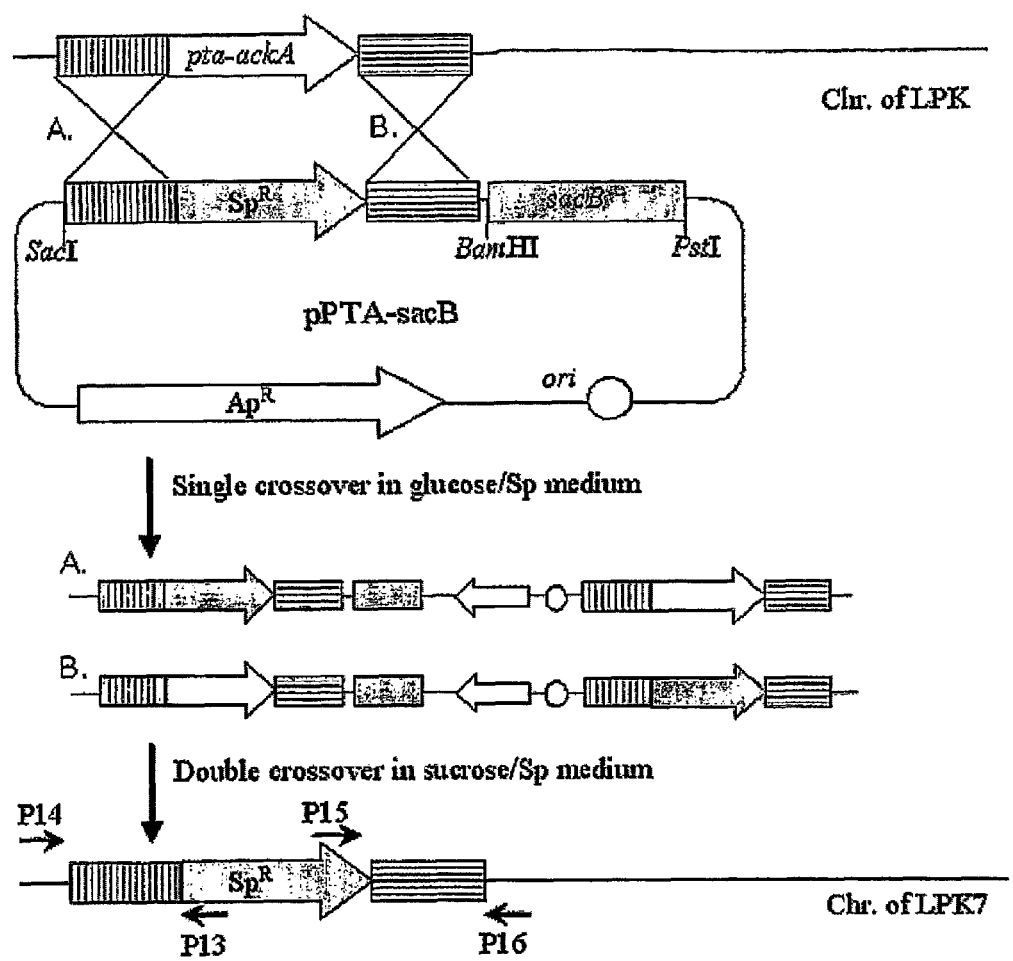
FIG. 8 shows a process of constructing bacterial mutant LPK7 by disrupting pta and ackA genes from *Mannheimia* sp. LPK.
Figure 9:
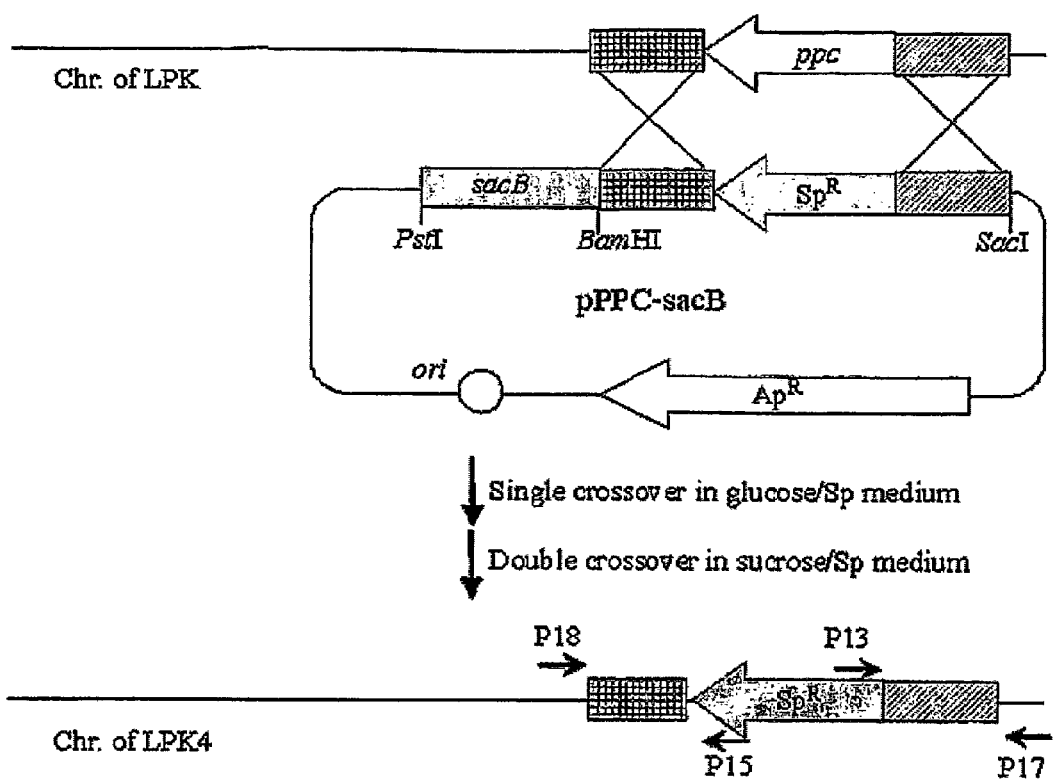
FIG. 9 shows a process of constructing bacterial mutant LPK4 by disrupting a ppc gene from *Mannheimia* sp. LPK.

FIG. 8 and FIG. 9 show processes of constructing mutant strains LPK7 and LPK4 by disrupting pta-ackA and ppc from *Mannheimia* sp. LPK, respectively. *Mannheimia* sp. LPK was plated on LB-glucose medium containing 10 g/l glucose, and cultured at 37° C. for 36 hours. The colony formed was inoculated in 10 ml LB-glucose liquid medium and cultured for 12 hours. The culture broth which had been sufficiently grown was inoculated by 1% in 100 ml LB-glucose liquid medium and cultured in a shaking incubator at 37° C.

Cell concentrate was collected from the resulting culture broth in the same manner as described in Example 3. The collected cell concentrate was mixed with the genetic exchange vectors pPTA-sacB and pPPC-sacB constructed in Examples 5 and 6, and then subjected to electroporation under conditions of 1.8 kV, 25° F. and 200 ohms. The electroporated mixture was added with 1 ml of LB-glucose liquid medium and cultured in a shaking incubator at 200 rpm and 37° C. for one hour.

The culture broth was plated on LB-glucose solid medium containing a spectinomycin antibiotic (final concentration: 50 (g/ml), and cultured at 37° C. for at least 48 hours. In order to select a colony where double crossover occurred, the colonies formed were streaked on LB-sucrose medium (LB medium containing 100 g/l of sucrose) containing 50 (g/ml of spectinomycin. After 24 hours, the formed colonies were re-streaked on the same plate. The colony (mutant) formed on the plate was cultured in LB-glucose liquid medium containing an antibiotic, and a genomic DNA was isolated from the cultured strain by the method of Rochelle et al. The isolated mutant genomic DNA as a template was amplified by PCR, and the PCR product was electrophoresed to confirm the disruption of each of pta-ackA and ppc.

To confirm the disruption of pta-ackA, PCRs were performed twice in the following manner. First, the mutant genomic DNA as a template was subjected to PCR using primers set forth in SEQ ID NO: 32 and SEQ ID NO: 33 below. Then, the mutant genomic DNA as a template was subjected to PCR using primers set forth in SEQ ID NO: 34 and SEQ ID NO: 35.

```
SEQ ID NO: 32:
5'-CCTGCAGGCATGCAAGCTTGGGCTGCAGGTCGACTC

SEQ ID NO: 33:
5'-GCTGCCAAACAACCGAAAATACCGCAATAAACGGC

SEQ ID NO: 34:
5'-GCATGTAACTTTACTGGATATAGCTAGAAAAGGCATCGGGGAG

SEQ ID NO: 35:
5'-GCAACGCGAGGGTCAATACCGAAGGATTTCGCCG
```

Figure 10:
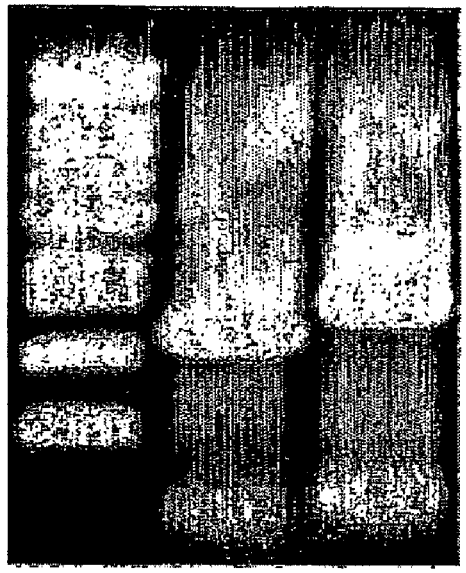
FIG. 10 is an electrophoresis photograph showing the disruption of pta and ackA genes from *Mannheimia* sp. LPK7 (M: 1-kb ladder size marker; lane 1: PCR product P13 & P14 (1.1 kb); and lane 2: PCR product P15 & P16 (1.5 kb)).

The products obtained in the two PCRs were subjected to gel electrophoresis to confirm the disruption of pta-ackA by their size (FIG. 10). In FIG. 10, M represents a 1-kb ladder size marker, lane 1 represents the PCR product P13 & P14 (1.1 kb), and lane 2 represents the PCR product P15 & P16 (1.5 kb). The disruption of pta-ackA was confirmed by the fact the product resulted from the PCR using the primers of SEQ ID NO: 32 and SEQ ID NO: 33 (P13 & P14) has a size of 1.1 kb at the same time the product resulted from the PCR using the primers of SEQ ID NO: 34 and SEQ ID NO: 35 (P15 & P16) has a size of 1.5 kb. The positions of the primers are shown in FIG. 8. The mutant strain constructed as described above, i.e., a strain resulted from the disruption of pta-ackA from *Mannheimia* sp. LPK, was named "*Mannheimia* sp. LPK7" and deposited under accession number "KCTC 10626BP" in KCTC, an international depositary authority.

Furthermore, to confirm the disruption of ppc, PCRs were performed twice in the following manner. First, the mutant genomic DNA as a template was subjected to PCR using primers set forth in SEQ ID NO: 32 and SEQ ID NPO: 36. Then, the mutant genomic DNA as a template was subjected to PCR using primers set forth in SEQ ID NO: 34 and SEQ ID NO: 37.

```
SEQ ID NO: 36:
5'-GATCCAGGGAATGGCACGCAGGCTTTCAACGCCGCC

SEQ ID NO: 37:
5'-GCAAAGCCAGAGGAATGGATGCCATTAACCAATAGCG
```

Figure 11:
FIG. 11 is an electrophoresis photograph showing the disruption of a ppc gene from *Mannheimia* sp. LPK4 (M: 1-kb ladder size marker; lane 1: PCR product P13 & P17 (1.1 kb); and lane 2: PCR product P15 & P18 (1.5 kb)).

The products obtained in the two PCRs were subjected to gel electrophoresis to confirm the disruption of ppc by their size (FIG. 11). In FIG. 11, M represents a 1-kb ladder size marker, lane 1 is the PCR product P13 & P17 (1.1 kb), and lane 2 represents the PCR product P15 & P18 (1.5 kb). The disruption of ppc was confirmed by the fact that the product resulted from the PCR using the primers of SEQ ID NO: 32 and SEQ ID NO: 36 (P13 & P17) has a size of 1.1 kb at the same time the product resulted from the PCR using the primers of SEQ ID NO: 34 and SEQ ID NO: 37 (P15 & P18) has a size of 1.5 kb. The positions of the primers are shown in FIG. 9. The mutant strain constructed as described above, i.e., a strain resulted from the disruption of ppc from *Mannheimia* sp. LPK, was named "*Mannheimia* sp. LPK4".

EXAMPLE 8

Fermentation Characteristics of LPK7 and LPK4

In order to examine the fermentation characteristics of *Mannheimia* sp. LPK7 and LPK4 constructed in Example 7 above, the mutant strains were cultured in anaerobic conditions saturated with $CO_2$, and the resulting reaction products were analyzed. First, carbon dioxide was introduced into 200 ml of the preculture medium as described in Example 4, and each of *Mannheimia* sp. LPK7 and LPK4 was inoculated in the preculture medium and precultured at 39° C. for 24 hours. Next, 1.8 L of a culture medium, which is the same as that in Example 4 except that glucose concentration is 18 g/L (final 100 mM), was put in a 6.6 L culture tank, and 100 ml of the precultured microorganisms was inoculated in the culture medium and then batch-cultured at 39° C. and pH 6.5 while supplying carbon dioxide at a flow rate of 0.25 vvm.

Figure 12:
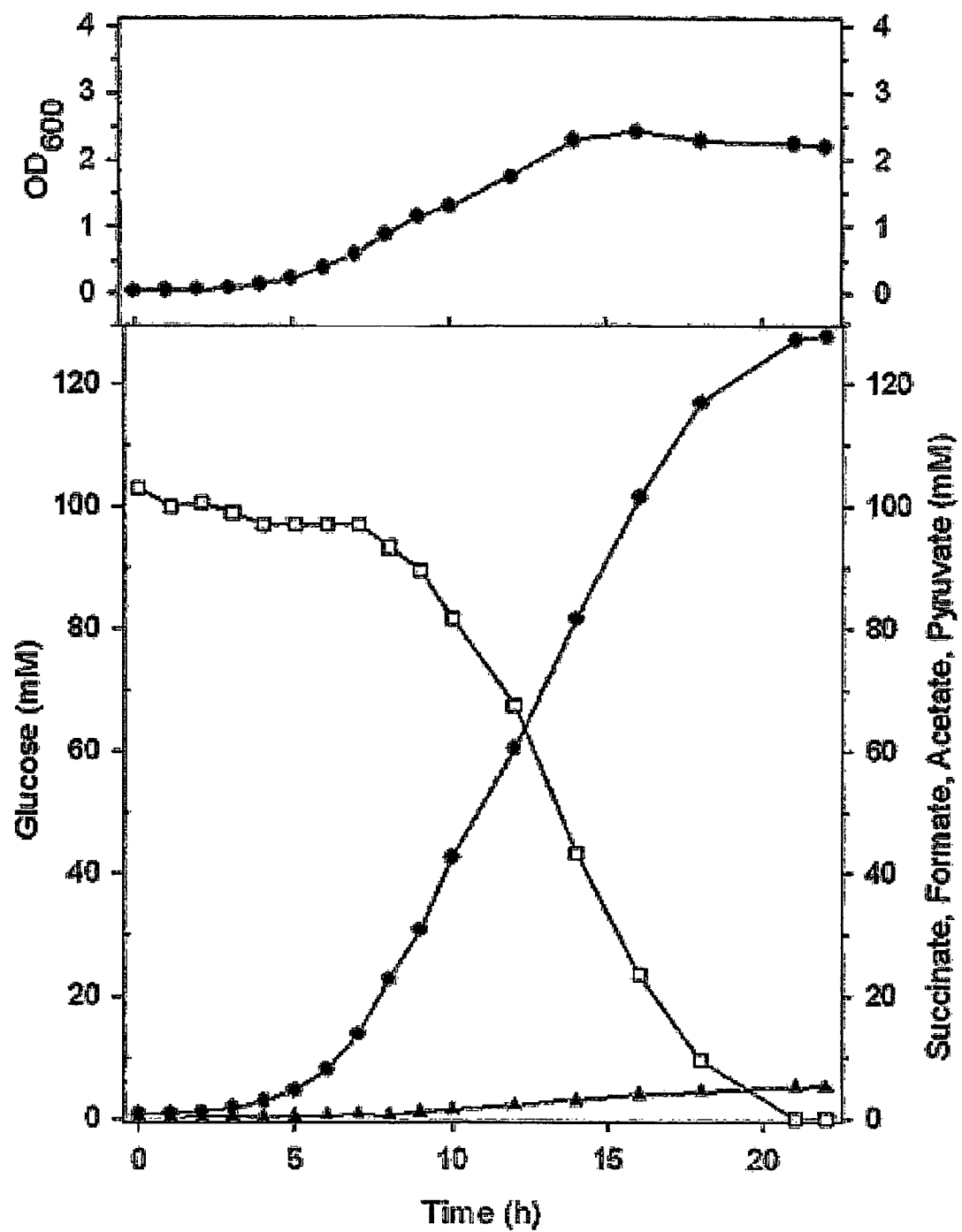
FIG. 12 shows the cultivation characteristics of *Mannheimia* sp. LPK7 in anaerobic conditions saturated with $CO_2$.
Figure 13:
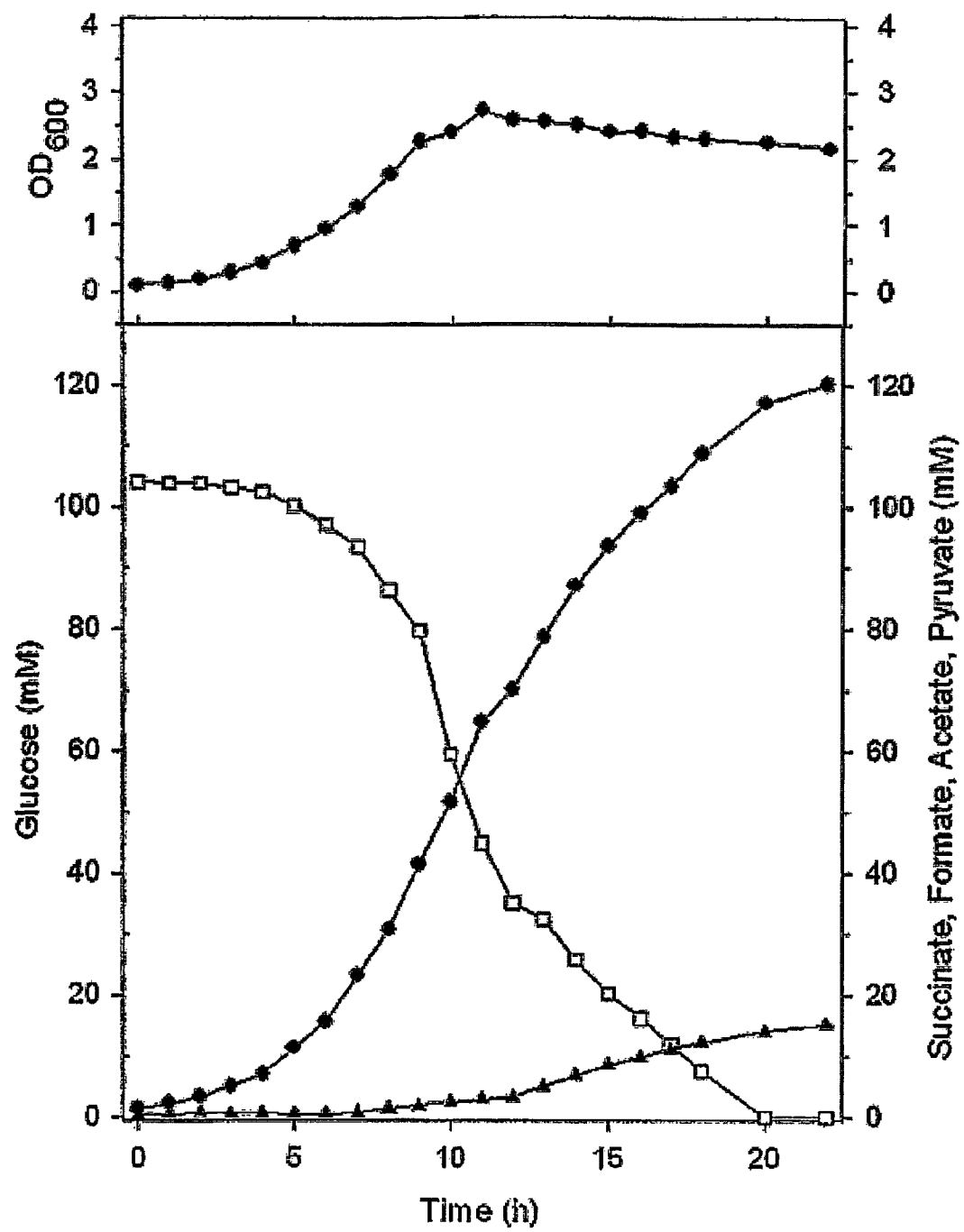
FIG. 13 shows the cultivation characteristics of *Mannheimia* sp. LPK4 in anaerobic conditions saturated with $CO_2$.

The concentrations of cells, succinate, glucose, lactate, acetate and formate were measured in the same manner as in Example 4 (FIG. 12 and FIG. 13). Symbols in FIG. 12 and FIG. 13 refer to changes in the concentrations of cells (● in upper portion), succinate (● in lower portion), glucose (□), formate (♦) and acetate (▲) with the passage of culture time. As shown in FIG. 12, after 22 hours of the culture of *Mannheimia* sp. LPK7, the concentration of consumed glucose was 100 mM and the concentration of produced succinate was 124 mM, indicating that the yield of succinate (the amount of produced succinate/the amount of consumed glucose) is 124 mol %. And, the production of acetate was remarkably reduced (Table 1). Also, as shown in FIG. 13, after 22 hours of the culture of *Mannheimia* sp. LPK4, the concentration of consumed glucose was 100 mM and the concentration of produced succinate was 123.7 mM, indicating that the yield of succinate (the amount of produced succinate/the amount of consumed glucose) is 123.7 mol %. And, the production of acetate was greatly reduced as compared to that in the wild type (Table 1).

The inventive method of producing succinic acid by culturing *Mannheimia* sp. LPK7 in anaerobic conditions saturated with $CO_2$ showed a great increase in the yield of succinic acid and also a 9.8 times increase in the ratio of succinic acid: acetic acid, as compared to that of producing succinic acid by culturing parent strain *Mannheimia succiniciproducens* 55E in anaerobic conditions saturated with $CO_2$, indicating that the inventive method can produce succinic acid with producing little or no byproducts (Table 1).

As reported by Bulter et al., even if acetate-producing genes in microorganisms known till now are all disrupted, a significant amount of acetate is produced in amino acid and fatty acid metabolisms which are still not established (Bulter et al. *PNAS*, 101:2299, 2004). Thus, the present invention cut off all acetate production pathways known till now, and achieved succinate fermentation at high yield and concentration.

TABLE 1

Comparison of products from fermentation of LPK4 and LPK7 and product from fermentation of 55E in anaerobic conditions

| Strain | Fermentation products (mM) | | | | | | S/A ratio (fold) |
| --- | --- | --- | --- | --- | --- | --- | --- |
| | Succinate | Acetate | Formate | Lactate | Pyruvate | Ethanol | |
| 55E | 99.1 | 40.6 | 53.8 | 8.2 | 13 | <1.0 | 2.44 (1.0) |
| LPK4 | 123.7 ± 6.2 | 28.1 ± 5.4 | ND | ND | 12.2 ± 6.3 | <1.0 | 4.40 (1.8) |
| LPK7 | 124.0 ± 5.2 | 5.2 ± 0.2 | ND | ND | 36.36 ± 4.7 | <1.0 | 23.84 (9.8) |

While the present invention has been described in detail with reference to the specific features, it will be apparent to persons skilled in the art that this description is only for a preferred embodiment and does not limit the scope of the present invention. Thus, the substantial scope of the present invention will be defined by the appended claims and equivalents thereof.

INDUSTRIAL APPLICABILITY

As described and provided above in detail, *Mannheimia* sp. mutant strains (LPK, LPK7 and LPK4) produce succinic acid in anaerobic conditions saturated with $CO_2$ and are facultative anaerobic strains having high resistance to oxygen. Thus, the production of succinic acid using such mutants can not only eliminate the fermentation process instability caused by oxygen exposure, etc., but also eliminate the production of other organic acids, as compared to the prior method of producing succinic acid using obligate anaerobic strains, thereby making it possible to optimize and maximize a purification process and production yield.

What is claimed is:

1. A rumen bacterial mutant in which a lactate dehydrogenase-encoding gene (ldhA), a pyruvate formate-lyase-encoding gene (pfl), a phosphotransacetylase-encoding gene (pta) and a acetate kinase-encoding gene (ackA) have been disrupted, and which has the property of producing succinic acid in anaerobic conditions, wherein the rumen bacteria are selected from the group consisting of the genus *Mannheimia*, the genus *Actinobacillus* and the genus *Anaerobiospirillum*.

2. The rumen bacterial mutant according to claim 1, wherein the rumen bacterial mutant is *Mannheimia* sp. LPK7.

3. The rumen bacterial mutant according to claim 2, wherein said *Mannheimia* sp. LPK7 is KCTC 10626BP.

4. A method for producing rumen bacterial mutant that has the property of producing succinic acid at high concentration while producing no other organic acids relative to wild type in anaerobic conditions, the method further comprising disrupting a phosphotransacetylase-encoding gene (pta) and an acetate kinase-encoding gene (ackA) from rumen bacteria that are selected from the group consisting of genus *Mannheimia*, genus *Actinobacillus* and genus *Anaerobiospirillum*, and a lactate dehydrogenase-encoding gene (ldhA) and a pyruvate formate-lyase-encoding gene (pfl) have been disrupted.

5. The method for producing the rumen bacterial mutant according to claim 4, wherein the rumen bacterial mutant having disruptions of a lactate dehydrogenase-encoding gene (ldhA) and a pyruvate formate-lyase-encoding gene (pfl) is *Mannheimia* sp. LPK (KCTC 10558BP).

6. The method for producing the rumen bacterial mutant according to claim 4, wherein the disruption of the pta and ackA genes is performed by homologous recombination.

7. The method for producing the rumen bacterial mutant according to claim 6, wherein the homologous recombination is performed using a genetic exchange vector containing a disrupted pta and ackA.

8. The method for producing the rumen bacterial mutant according to claim 7, wherein the genetic exchange vector containing a disrupted pta and ackA is pPTA-sacB.

9. The rumen bacterial mutant according to claim 1, wherein the rumen bacteria are homo-fermentative bacteria that produce succinic acid.

\* \* \* \* \*

UNITED STATES PATENT AND TRADEMARK OFFICE
CERTIFICATE OF CORRECTION

PATENT NO.        : 7,470,530 B2
APPLICATION NO.   : 10/580556
DATED             : December 30, 2008
INVENTOR(S)       : Sang Yup Lee It is certified that error appears in the above-identified patent and that said Letters Patent is hereby corrected as shown below:

Title Page and Col. 1
Title of the Invention: "RUMEN BACTERIA VARIANTS AND PROCESS OF PREPARING SUCCINIC ACID EMPLOYING THE SAME" should be -- NOVEL RUMEN BACTERIA VARIANTS AND PROCESS OF PREPARING SUCCINIC ACID EMPLOYING THE SAME --.

Title page, first column, References Cited, add: -- U.S. PATENT DOCUMENTS --.

Title page, first column, References Cited, U.S. PATENT DOCUMENTS, add: -- 5,143,833 A  9/1992  Datta --.

Title page, first column, References Cited, U.S. PATENT DOCUMENTS, add: -- 5,521,075 A  5/1996  Guettler, et al. --.

Title page, second column, ABSTRACT, fifth line; "pfl,a" should be -- pfl, a --.

Column 2, line 33: "(ackA,)" -- (ackA), --.

Signed and Sealed this

Seventh Day of April, 2009

JOHN DOLL
*Acting Director of the United States Patent and Trademark Office*

SEQUENCE LISTING

<160> NUMBER OF SEQ ID NOS: 37

<210> SEQ ID NO 1
<211> LENGTH: 30
<212> TYPE: DNA
<213> ORGANISM: Artificial
<220> FEATURE:
<223> OTHER INFORMATION: Primer LS1

<400> SEQUENCE: 1
cagtgaagga gctccgtaac gcatccgccg                              30

<210> SEQ ID NO 2
<211> LENGTH: 30
<212> TYPE: DNA
<213> ORGANISM: Artificial
<220> FEATURE:
<223> OTHER INFORMATION: Primer LP1

<400> SEQUENCE: 2
ctttatcgaa tctgcaggcg gtttccaaaa                              30

<210> SEQ ID NO 3
<211> LENGTH: 30
<212> TYPE: DNA
<213> ORGANISM: Artificial
<220> FEATURE:
<223> OTHER INFORMATION: Primer LP2

```
<400> SEQUENCE: 3
gtactgtaaa ctgcagcttt catagttagc                                30

<210> SEQ ID NO 4
<211> LENGTH: 30
<212> TYPE: DNA
<213> ORGANISM: Artificial
<220> FEATURE:
<223> OTHER INFORMATION: Primer LH2

<400> SEQUENCE: 4
gccgaaagtc aagcttgccg tcgtttagtg                                30

<210> SEQ ID NO 5
<211> LENGTH: 10
<212> TYPE: DNA
<213> ORGANISM: Artificial
<220> FEATURE:
<223> OTHER INFORMATION: Linker 1

<400> SEQUENCE: 5
tctagaagct                                                      10

<210> SEQ ID NO 6
<211> LENGTH: 29
<212> TYPE: DNA
<213> ORGANISM: Artificial
<220> FEATURE:
<223> OTHER INFORMATION: Primer SXF

<400> SEQUENCE: 6
gctctagacc ttctatcgcc ttcttgacg                                 29

<210> SEQ ID NO 7
<211> LENGTH: 29
<212> TYPE: DNA
<213> ORGANISM: Artificial
<220> FEATURE:
<223> OTHER INFORMATION: Primer SXR

<400> SEQUENCE: 7
gctctagagg ctacaaaatc acgggcgtc                                 29

<210> SEQ ID NO 8
<211> LENGTH: 30
<212> TYPE: DNA
<213> ORGANISM: Artificial
<220> FEATURE:
<223> OTHER INFORMATION: Primer SBG

<400> SEQUENCE: 8
agcggatccc cttctatcgc cttcttgacg                                30

<210> SEQ ID NO 9
<211> LENGTH: 30
<212> TYPE: DNA
<213> ORGANISM: Artificial
<220> FEATURE:
<223> OTHER INFORMATION: Primer SPR

<400> SEQUENCE: 9
gtcctgcagg gctacaaaat cacgggcgtc                                30

<210> SEQ ID NO 10
<211> LENGTH: 30
```

```
<212> TYPE: DNA
<213> ORGANISM: Artificial
<220> FEATURE:
<223> OTHER INFORMATION: Primer PB1

<400> SEQUENCE: 10
catggcggat ccaggtacgc tgatttcgat                                      30

<210> SEQ ID NO 11
<211> LENGTH: 30
<212> TYPE: DNA
<213> ORGANISM: Artificial
<220> FEATURE:
<223> OTHER INFORMATION: Primer PB2

<400> SEQUENCE: 11
caaggatcca acggataaag cttttattat                                      30

<210> SEQ ID NO 12
<211> LENGTH: 30
<212> TYPE: DNA
<213> ORGANISM: Artificial
<220> FEATURE:
<223> OTHER INFORMATION: Primer CTR

<400> SEQUENCE: 12
ctcgagcccg gggtttaagg gcaccaataa                                      30

<210> SEQ ID NO 13
<211> LENGTH: 30
<212> TYPE: DNA
<213> ORGANISM: Artificial
<220> FEATURE:
<223> OTHER INFORMATION: Primer CTF

<400> SEQUENCE: 13
ctcgagcccc gggctttgcg ccgaataaat                                      30

<210> SEQ ID NO 14
<211> LENGTH: 22
<212> TYPE: DNA
<213> ORGANISM: Artificial
<220> FEATURE:
<223> OTHER INFORMATION: Primer KM1

<400> SEQUENCE: 14
gacgtttccc gttgaatatg gc                                              22

<210> SEQ ID NO 15
<211> LENGTH: 24
<212> TYPE: DNA
<213> ORGANISM: Artificial
<220> FEATURE:
<223> OTHER INFORMATION: Primer LU1

<400> SEQUENCE: 15
cattgaggcg tattatcagg aaac                                            24

<210> SEQ ID NO 16
<211> LENGTH: 23
<212> TYPE: DNA
<213> ORGANISM: Artificial
<220> FEATURE:
<223> OTHER INFORMATION: Primer KM2

<400> SEQUENCE: 16
```

```
gcagtttcat tgatgctccg atg                                         23

<210> SEQ ID NO 17
<211> LENGTH: 24
<212> TYPE: DNA
<213> ORGANISM: Artificial
<220> FEATURE:
<223> OTHER INFORMATION: Primer LD2

<400> SEQUENCE: 17
cctcttacga tgacgcatct ttcc                                        24

<210> SEQ ID NO 18
<211> LENGTH: 30
<212> TYPE: DNA
<213> ORGANISM: Artificial
<220> FEATURE:
<223> OTHER INFORMATION: Primer CM1

<400> SEQUENCE: 18
ggtggtatat ccagtgattt ttttctccat                                  30

<210> SEQ ID NO 19
<211> LENGTH: 28
<212> TYPE: DNA
<213> ORGANISM: Artificial
<220> FEATURE:
<223> OTHER INFORMATION: Primer PU1

<400> SEQUENCE: 19
ctttgcaaca ttatggtatg tattgccg                                    28

<210> SEQ ID NO 20
<211> LENGTH: 30
<212> TYPE: DNA
<213> ORGANISM: Artificial
<220> FEATURE:
<223> OTHER INFORMATION: Primer CM2

<400> SEQUENCE: 20
tactgcgatg agtggcaggg cggggcgtaa                                  30

<210> SEQ ID NO 21
<211> LENGTH: 26
<212> TYPE: DNA
<213> ORGANISM: Artificial
<220> FEATURE:
<223> OTHER INFORMATION: Primer PD2

<400> SEQUENCE: 21
ccccagcatg tgcaaatctt cgtcac                                      26

<210> SEQ ID NO 22
<211> LENGTH: 32
<212> TYPE: DNA
<213> ORGANISM: Artificial
<220> FEATURE:
<223> OTHER INFORMATION: Primer

<400> SEQUENCE: 22
gctctagata tccgcagtat cactttctgc gc                               32

<210> SEQ ID NO 23
<211> LENGTH: 30
<212> TYPE: DNA
<213> ORGANISM: Artificial
```

```
<220> FEATURE:
<223> OTHER INFORMATION: Primer

<400> SEQUENCE: 23
tccgcagtcg gatccgggtt aaccgcacag                                30

<210> SEQ ID NO 24
<211> LENGTH: 39
<212> TYPE: DNA
<213> ORGANISM: Artificial
<220> FEATURE:
<223> OTHER INFORMATION: Primer

<400> SEQUENCE: 24
ggggagctcg ctaacttagc ttctaaaggc catgtttcc                      39

<210> SEQ ID NO 25
<211> LENGTH: 32
<212> TYPE: DNA
<213> ORGANISM: Artificial
<220> FEATURE:
<223> OTHER INFORMATION: Primer

<400> SEQUENCE: 25
gctctagata tccgggtcaa tatcgccgca ac                             32

<210> SEQ ID NO 26
<211> LENGTH: 30
<212> TYPE: DNA
<213> ORGANISM: Artificial
<220> FEATURE:
<223> OTHER INFORMATION: Primer

<400> SEQUENCE: 26
gaattcgagc tcgcccgggg atcgatcctc                                30

<210> SEQ ID NO 27
<211> LENGTH: 36
<212> TYPE: DNA
<213> ORGANISM: Artificial
<220> FEATURE:
<223> OTHER INFORMATION: Primer

<400> SEQUENCE: 27
cccgggccga caggctttga agcatgcaaa tgtcac                         36

<210> SEQ ID NO 28
<211> LENGTH: 32
<212> TYPE: DNA
<213> ORGANISM: Artificial
<220> FEATURE:
<223> OTHER INFORMATION: Primer

<400> SEQUENCE: 28
tacggatccc cagaaaatcg cccccatgcc ga                             32

<210> SEQ ID NO 29
<211> LENGTH: 37
<212> TYPE: DNA
<213> ORGANISM: Artificial
<220> FEATURE:
<223> OTHER INFORMATION: Primer

<400> SEQUENCE: 29
gctctagata tcgtttgata ttgttccgcc acatttg                        37
```

<210> SEQ ID NO 30
<211> LENGTH: 36
<212> TYPE: DNA
<213> ORGANISM: Artificial
<220> FEATURE:
<223> OTHER INFORMATION: Primer

<400> SEQUENCE: 30
gctctagata tccgtcagga aagcacccgc catagc                                36

<210> SEQ ID NO 31
<211> LENGTH: 39
<212> TYPE: DNA
<213> ORGANISM: Artificial
<220> FEATURE:
<223> OTHER INFORMATION: Primer

<400> SEQUENCE: 31
ggggagctcg tgtggcgctg cggaagtaag gcaaaaatc                             39

<210> SEQ ID NO 32
<211> LENGTH: 36
<212> TYPE: DNA
<213> ORGANISM: Artificial
<220> FEATURE:
<223> OTHER INFORMATION: Primer

<400> SEQUENCE: 32
cctgcaggca tgcaagcttg ggctgcaggt cgactc                                36

<210> SEQ ID NO 33
<211> LENGTH: 35
<212> TYPE: DNA
<213> ORGANISM: Artificial
<220> FEATURE:
<223> OTHER INFORMATION: Primer

<400> SEQUENCE: 33
gctgccaaac aaccgaaaat accgcaataa acggc                                 35

<210> SEQ ID NO 34
<211> LENGTH: 43
<212> TYPE: DNA
<213> ORGANISM: Artificial
<220> FEATURE:
<223> OTHER INFORMATION: Primer

<400> SEQUENCE: 34
gcatgtaact ttactggata tagctagaaa aggcatcggg gag                        43

<210> SEQ ID NO 35
<211> LENGTH: 34
<212> TYPE: DNA
<213> ORGANISM: Artificial
<220> FEATURE:
<223> OTHER INFORMATION: Primer

<400> SEQUENCE: 35
gcaacgcgag ggtcaatacc gaaggatttc gccg                                  34

<210> SEQ ID NO 36
<211> LENGTH: 36
<212> TYPE: DNA
<213> ORGANISM: Artificial
<220> FEATURE:
<223> OTHER INFORMATION: Primer

<400> SEQUENCE: 36
gatccaggga atggcacgca ggctttcaac gccgcc                                    36

<210> SEQ ID NO 37
<211> LENGTH: 37
<212> TYPE: DNA
<213> ORGANISM: Artificial
<220> FEATURE:
<223> OTHER INFORMATION: Primer

<400> SEQUENCE: 37
gcaaagccag aggaatggat gccattaacc aatagcg                                   37